(12) United States Patent
Mulier et al.

(10) Patent No.: US 6,328,736 B1
(45) Date of Patent: Dec. 11, 2001

(54) FLUID-ASSISTED ELECTROCAUTERY DEVICE

(75) Inventors: Peter M. J. Mulier, St. Paul; Michael F. Hoey, Shoreview, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/507,961

(22) Filed: Feb. 22, 2000

Related U.S. Application Data

(63) Continuation of application No. 08/393,082, filed on Feb. 22, 1995, now Pat. No. 6,063,081.

(51) Int. Cl.[7] .................................................. A61B 18/14
(52) U.S. Cl. ................................ 606/45; 606/49; 604/35
(58) Field of Search .................................. 606/25, 41, 42, 606/45, 46, 48–50; 604/35; 607/145, 153

(56) References Cited

U.S. PATENT DOCUMENTS

| | | | |
|---|---|---|---|
| 3,163,166 | * | 12/1964 | Brant ..................................... 607/145 |
| 3,901,241 | * | 8/1975 | Allen, Jr. ................................ 606/25 |
| 4,602,628 | * | 7/1986 | Allen, Jr. ................................ 606/25 |
| 5,122,138 | * | 6/1992 | Manwaring ............................. 606/46 |
| 5,167,659 | * | 12/1992 | Ohtomo et al. ........................ 606/40 |
| 5,458,596 | * | 10/1995 | Lax et al. ............................... 606/31 |

\* cited by examiner

Primary Examiner—Lee Cohen
(74) Attorney, Agent, or Firm—Harold R Patton; Daniel W. Latham

(57) ABSTRACT

An electrocautery instrument is provided with a hollow electrode having a source of conductive fluid coupled to a proximal end thereof. Conductive fluid is communicated through said electrode and expelled out of the distal end thereof during electrocautery, forming a "virtual electrode." The infused conductive liquid conducts the RF electrocautery energy away from the conductive electrode, thereby displacing the region of thermal generation and reducing the extent of burns and perforations caused by conventional electrocautery electrodes. In one embodiment, the electrode is partially disposed within and extends distally out of a retractable suction tube, such that smoke and fluid are aspirated from the electrocautery site. When the suction tube is fully advanced. the electrode is concealed therein, enabling suction without electrocautery to be performed.

20 Claims, 2 Drawing Sheets

FLUID-ASSISTED ELECTROCAUTERY DEVICE

CROSS-REFERENCE TO RELATED APPLICATIONS

This application is a continuation of U.S. Ser. No. 08/393,082, filed Feb. 22, 1995, now U.S. Pat. No. 6,063,081, the entire disclosure of which is incorporated herein by reference.

FIELD OF THE INVENTION

This invention relates generally to the field of medical instruments, and more particularly relates to an electrocautery device.

BACKGROUND OF THE INVENTION

Various types of electrocautery devices for incising and cauterizing body tissue are known and used in the medical field. Typically, such devices include a conductive blade or needle which serves as one electrode in an electrical circuit which is completed via a grounding electrode coupled to the patient. Incision of tissue is accomplished by applying a source of electrical energy (most commonly, a radio-frequency generator) to the blade. Upon application of the blade to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

It is widely recognized in the prior art that the often substantial amount of smoke produced by electrocauterization of tissue is at least unpleasant, and in some cases distracting or even hazardous to the operator and other attending medical personnel. As a result, it has been proposed, and is common, to provide an electrocautery device with smoke-aspirating capabilities, such that the smoke produced from electrocauterization is quickly withdrawn from the area of incision. Smoke aspiration may be accomplished by providing, in the handle of the electrocautery device near the electrocautery blade/electrodes an inlet port to be coupled to a vacuum or suction source. Examples of this are described in U.S. Pat. No. 4,307,720 to Weber, Jr., entitled "Electrocautery Apparatus and Method and Means for Cleaning the Same;" in U.S. Pat. No. 5,242,442 to Hirschfeld, entitled "Smoke Aspirating Electrosurgical Device;" and in U.S. Pat. No. 5,269,781 to Hewell, entitled "Suction Assisted Electrocautery Unit."

It has also been recognized in the prior art that the accumulation of coagulated blood, tissue rubble, and other debris on the electrode/blade of an electrocautery device can present a problem for the operator, necessitating the periodic cleaning of the blade, e.g., by wiping the blade over sterilized gauze or the like. This is generally regarded as undesirable, since the need to clean the electrode/blade tends to interrupt the incision procedure and increases the risks associated with contamination of the blade or the incision, damage to the blade, injury to the operator, and the like. To address this problem, it has been proposed in the prior art to provide an electrocautery instrument in which the electrode/blade is in slidable engagement with the instrument's handle, such that when the blade is retracted into the hand, any adhering debris automatically scraped off onto the tip of the handle. Such an instrument is proposed in the above-referenced Weber, Jr. '720 patent. While this arrangement may have some benefit, it still may be necessary to wipe off the tip of the handle once the blade is retracted. It is believed that a more direct and effective approach to the problem would be to reduce the amount of debris created during the electrocautery process, thereby eliminating or at least reducing the need to clean the electrode/blade.

SUMMARY OF THE INVENTION

In view of the foregoing considerations, the present invention is directed to an improved electrocautery instrument.

In one embodiment of the invention, an electrocautery instrument is configured with an electrode/blade disposed within a retractable suction tube, such that with the suction tube advanced, the electrode/blade is concealed within the tube, and with the suction tube retracted, the distal end of the electrode/blade is exposed for performing electrocautery.

In accordance with one aspect of the invention, the electrocautery electrode/blade is implemented with a hollow, conductive tube, flattened at it distal end into a blade-like configuration. Conductive fluid is applied to the proximal end of the hollow electrode/blade, and expelled from the distal (blade) end thereof during electrocautery. In accordance with another aspect of the invention, the conductive fluid emanating from the electrode/blade conducts the RF electrocautery energy away from the blade, so that it is primarily the fluid, rather than the metal blade, which actually accomplishes the cutting of tissue. That is, the fluid serves as a "virtual" electrocautery electrode. Since it is the fluid, rather than the blade, which incises and cauterizes, no burns or perforations are made to the tissue, reducing the amount of debris in the incision. Also, the flow of fluid through the electrode/blade tends to keep the blade clean and cool.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
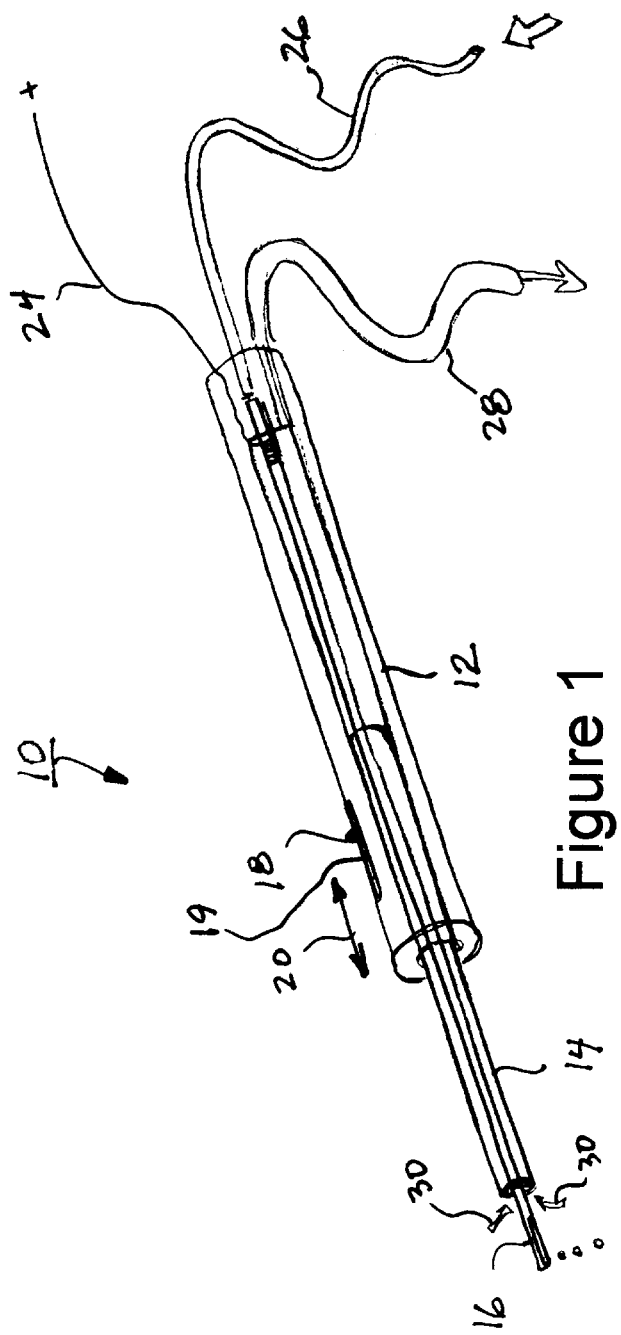
FIG. 1 is a perspective view of an electrocautery instrument in accordance with one embodiment of the invention.

Referring, to FIG. 1, there is shown a perspective view of a fluid-assisted electrocautery instrument 10 in accordance with one embodiment of the invention. Electrocautery instrument 10 comprises a handle 12, a suction tube 14, and an electrocautery electrode/blade 16. Handle 12 is preferably made of a sterilizable, rigid, and non-conductive material, such as nylon or the like. Suction tube 13, which is also preferably made of a sterilizable and non-conductive material, is slidably disposed partially within an internal lumen of handle 12, and projects distally, out of the end thereof. Electrode/blade 16 is disposed within suction tube 14 and handle 12. Suction tube 14 is adapted to slide proximally and distally with respect to handle 12 and electrode 16 (i.e., in the directions of arrow 20 in FIG. 1) by means of a sliding lever 18 extending out of a slot 19 in handle 12. With suction tube 14 in a retracted position, as shown in FIG. 1, a distal portion of electrode/blade 16 projects beyond the distal end of tube 14, such that electrocautery can be performed. With suction tube in an advanced position, suction tube 14 completely conceals the tip of electrode/blade 16.

Figure 2:
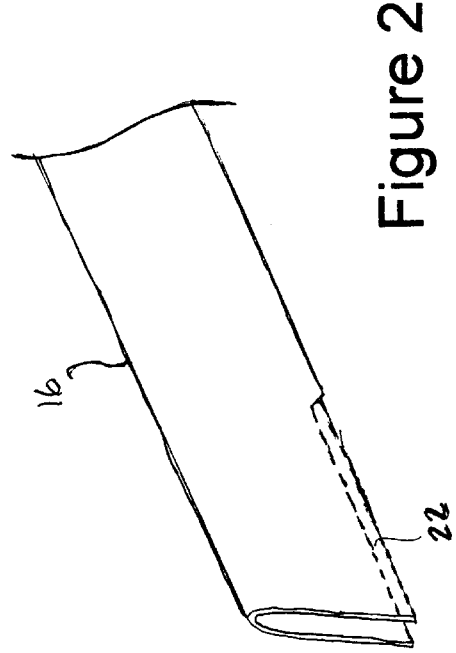
FIG. 2 is a enlarged perspective view of the distal end of the electrode/blade of the electrocautery instrument of FIG. 1.

In accordance with one aspect of the invention, electrode/blade 16 is preferably implemented using a hollow cylindrical tube which has been flatted at its distal end, as shown in the greatly enlarged perspective view of FIG. 2. In addition to being flattened, a portion of the distal end of electrode/blade 16 is removed to form a longitudinal slit 22 therein.

Three connections are made to electrocautery instrument 10: One terminal (e.g., positive) of a radio-frequency (RF) generator (not shown in FIG. 1) is electrically coupled to electrode/blade 16 via a wire 24; a source of fluid to be expelled from slit 22 in electrode/blade 16 is coupled to the proximal end of electrode/blade 16 via a flexible tube or hose 26; and a suction hose 28 is coupled to handle 12 so as to be in communication with the internal lumen of handle 12 and with suction tube 14. When suction is applied via hose 28, air and fluid are drawn into the distal end of suction tube 14, as indicated by arrows 30. The ability to advance or retract suction tube 14 with respect to electrode/blade 16 enables the operator of the instrument to perform electrocautery while simultaneously aspirating smoke and fluid from the incision site, or to use suction tube 14 alone, without performing electrocautery.

As noted above, conductive fluid is communicated from inflow tube 26 and communicated along the length of electrode/blade 16 to be expelled from the distal end thereof. This is done in order to establish a so-called virtual electrode for performing electrocautery. The infusion of conductive fluid simultaneously with the application of RF energy is discussed in further detail in: U.S. patent application Ser. No. 08/113,441 entitled "Method and Apparatus for R-F Ablation," filed on Aug. 27, 1993 in the name of Peter M. J. Mulier and Michael F. Hoey, in U.S. patent application Ser. No. 08/303,246, entitled "Method and Apparatus for RF Ablation," filed on Sep. 8, 1994 in the name of Peter M. J. Mulier; and in U.S. patent application Ser. No. 08/302,304 entitled "Method and Apparatus for RF Ablation," filed in the name of Peter M. J. Mulier and Michael F. Hoey on Sep. 8, 1994. The foregoing '441 '246, and '304 applications (hereinafter collectively referred to as "the RF ablation applications") are each commonly assigned to the assignee of the present invention, and incorporated by reference herein in their respective entireties.

As described in the RF ablation patents, the infusion of conducting fluid into the area of application of RF energy creates a "virtual electrode," the size and shape of which can be controllably modified, and which can be rendered more or less conductive, thereby modifying the spread of RF energy. By varying such factors as the RF energy and duration, the rate of infusion of conductive liquid, and the conductivity of the infused solution, the size, shape, and intensity of the "virtual electrode"—i.e., the intensity of thermal production in the area, can be controlled. In the case of the electrocautery device in accordance with the present invention, application of the conductive solution during the application of RF energy further assists by preventing overheating of the electrode/blade, extending the point at which burning or charring of tissue would otherwise normally occur. To enhance this effect, it is contemplated that the solution being infused may first be cooled.

Figure 3:
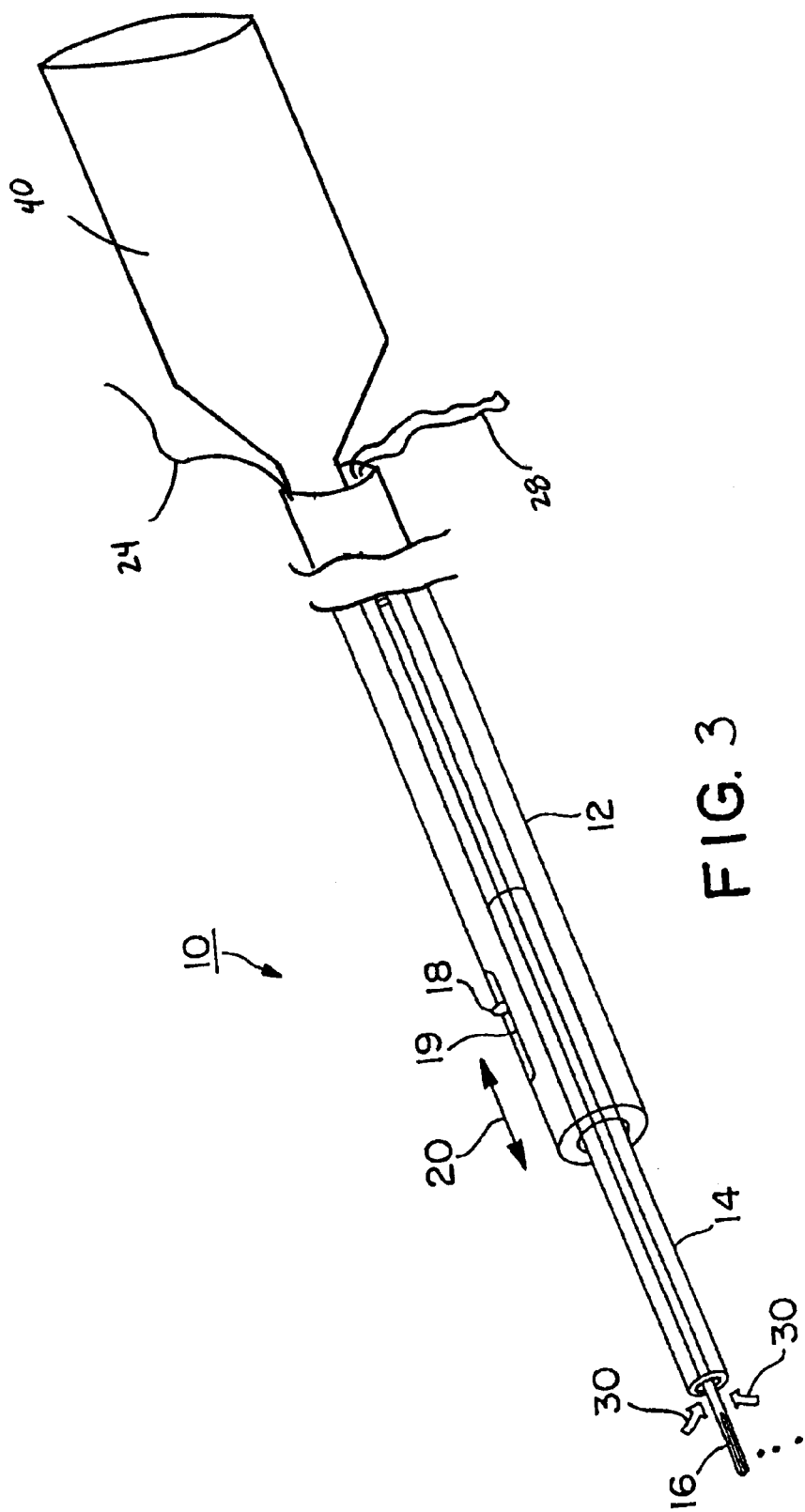
FIG. 3 is a perspective view of an alternative embodiment electrocautery instrument.

Conductive solutions believed to be suitable for establishing the virtual electrode include saline, saturated saline, and Ringer's solution, among others. Regarding the source of conductive fluid, it is contemplated that a conventional pump may be coupled to input line 26. Alternatively, it is contemplated that a small, pre-pressurized canister of conductive solution may be used, such that no pump is required. In one embodiment, as shown in FIG. 3, handle 12 may be configured to receive such a pressurized canister 40 therein, eliminating the need for input line 26.

Although in the embodiment of FIG. 1, input line 26, suction line 28, and electrical connection 24 are depicted separately, it is contemplated that these connections to instrument 10 may be consolidated into a single line having two separate fluid-conducting lumens therein (one for input of conductive solution, one for suction), alongside an insulated electrical conductor.

Various alternate configurations of electrode/blade 16 are also contemplated. In one embodiment, a porous metal element is substituted for the flattened tube configuration of FIGS. 1 and 2.

From the foregoing detailed description of a specific embodiment of the invention, it should be apparent that a method and apparatus for performing fluid-assisted electrocautery of body tissue has been disclosed, wherein fluid delivered out of a hollow electrocautery electrode/blade creates a virtual electrode which incises and cauterizes the tissue.

Although a specific embodiment of the invention has been described herein, this has been done solely for the purposes of illustrating various aspects of the invention, and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims, which follow.

What is claimed is:

1. An electrocautery instrument comprising:
   a handle having proximal and distal ends;
   an electrode, the electrode in contact with the handle and being adapted to be coupled to a source of radiofrequency energy, the electrode having a distal end including a u-shaped configuration; and
   a lumen, the lumen in fluid communucation with the distal end of the electrode.

2. The electrocautery instrument according to claim 1 wherein the lumen is contained within the handle and extends between the proximal end of the handle and the distal end of the electrode.

3. The electrocautery instrument according to claim 1 further including a suction tube associated with the handle.

4. The electrocautery instrument according to claim 3 wherein the suction tube is longitudinally movable between a retracted position and an advanced position.

5. The electrocautery instrument according to claim 4 wherein the suction tube conceals the distal end of the electrode when the suction tube is in its advanced position.

6. The electrocautery instrument according to claim 1 further comprising a fluid source in fluid communication with the lumen.

7. The electrocautery instrument according to claim 6 further including a fluid input tube mounted at the proximal end of the handle and in communication with the lumen.

8. The electrocautery instrument according to claim 7 wherein the fluid source comprises a pump coupled to the input tube.

9. The electrocautery instrument according to claim 7 further including a suction tube associated with the handle.

10. The electrocautery instrument according to claim 6 wherein the fluid source comprises a canister containing a conductive solution and the canister being receivable within the handle.

11. The electrocautery instrument according to claim 10 wherein the canister is pre-pressurized.

12. An electrocautery instrument, comprising:

a handle;

an electrode blade adapted to be coupled to a source of radiofrequency energy, the electrode including a lumen, at least a portion of the electrode extending distal the handle; and a fluid source in communication with the lumen of the electrode, the fluid source comprising a canister of conductive solution that is received within the handle.

13. The electrocautery instrument according to claim 12 wherein the canister is pre-pressurized.

14. The electrocautery instrument according to claim 12 wherein the electrode has a distal end including a u-shaped configuration.

15. The electrocautery instrument according to claim 14 further comprising a suction tube disposed partially within the handle.

16. The electrocautery instrument according to claim 12 wherein the conductive fluid source is cooled.

17. A system for providing fluid to an electrocautery instrument comprising:

an electrode having a distal end and adapted to be coupled to a source of radiofrequency energy;

a lumen in fluid communication with the distal end of the electrode; and a fluid source comprising a canister of conductive solution in communication with the lumen.

18. The system according to claim 17 wherein the canister is pre-pressurized.

19. The system according to claim 17 further comprising a handle, wherein the canister of conductive solution is received within the handle.

20. The system according to claim 17 wherein the electrode has a distal end including a u-shaped configuration.

\* \* \* \* \*